United States Patent [19]

Saltzman et al.

[11] 4,311,485

[45] Jan. 19, 1982

[54] METHOD AND APPARATUS FOR PHOTOMETRICALLY MONITORING THE CONCENTRATIONS OF BOTH CHLORINE AND CHLORINE DIOXIDE

[75] Inventors: Robert S. Saltzman, Wilmington, Del.; James W. Williams, San Jose, Calif.

[73] Assignee: E. I. Du Pont de Nemours and Company, Wilmington, Del.

[21] Appl. No.: 220,200

[22] Filed: Dec. 23, 1980

[51] Int. Cl.³ .................. G01N 20/01; G01N 33/34
[52] U.S. Cl. ........................... 23/230 R; 23/230 A; 23/230 PC; 422/62; 422/80; 422/91
[58] Field of Search .......... 23/230 A, 230 R, 230 PC; 422/62, 91, 78, 80; 423/478

[56] References Cited

U.S. PATENT DOCUMENTS

| | | | |
|---|---|---|---|
| 3,306,156 | 2/1967 | Glasser et al. | 356/407 X |
| 4,152,073 | 5/1979 | Zimmerman | 356/436 |
| 4,251,224 | 2/1981 | Cowley et al. | 23/230 A |
| 4,251,503 | 2/1981 | Swindells et al. | 23/230 A |

*Primary Examiner*—Ronald Serwin

[57] ABSTRACT

A method and an apparatus for photometrically analyzing a stream under test containing both chlorine and chlorine dioxide is characterized by heating a portion of the stream to decompose any chlorine dioxide therein into elemental chlorine. This heated portion of the stream is photometrically analyzed to determine the concentration of chlorine produced by the decomposition of chlorine dioxide, taking into account the concomitant dilution produced thereby.

5 Claims, 2 Drawing Figures

METHOD AND APPARATUS FOR PHOTOMETRICALLY MONITORING THE CONCENTRATIONS OF BOTH CHLORINE AND CHLORINE DIOXIDE

FIELD OF THE INVENTION

This invention relates to photometric analysis and, in particular, to a method and apparatus for photometrically monitoring the concentrations of both chlorine and chlorine dioxide in a stream under test.

DESCRIPTION OF THE PRIOR ART

Chlorine dioxide is useful as a bleaching agent for pulp used in the manufacture of white paper. It is typically produced in a generator using as a reactant chlorate, as derived from sodium chlorate for example, in accordance with the following reaction:

$$4H^+ + 2Cl^- + 2ClO_3^- \rightarrow Cl_2 + 2ClO_2 + 2H_2O.$$

Ideally, two moles of chlorine dioxide are formed for every mole of chlorine. However, it is possible that side reactions can occur which will produce chlorine without producing any chlorine dioxide. For example, chlorate may combine with the chlorine ion to form chlorine and water in accordance with the following reaction:

$$6H^+ + 5Cl^- + ClO_3^- \rightarrow 3Cl_2 + 3H_2O.$$

This reaction is undesirable since it decreases the overall yield of chlorine dioxide, the desired end product. Thus, the overall reaction is rendered less efficient and requires a greater energy expenditure to produce the same amount of chlorine dioxide. For at least this reason it is desirable to monitor the production of chlorine and chlorine dioxide to insure that the ratio of these products is maintained within predetermined limits so that the reaction efficiency is optimized.

Additionally, it is known that when the chloride dioxide concentration in air exceeds fifteen percent, it is explosive. It is, therefore, important to monitor the generator to insure that the concentration of chlorine dioxide lies within a predetermined range, usually between ten and twelve percent.

The article "Continuous Monitoring For Control of Chlorine Dioxide Generators" written by R. S. Saltzman and published in "Instrumentation in the Pulp and Paper Industry", Volume 16, Section 609, Coden:IP-PICO 16 (1975), Instrument Society of America, Research Triangle Park, North Carolina, describes a photometric analysis apparatus adapted to continuously monitor the output of a chlorine dioxide generator to insure that the concentration of chlorine dioxide produced therein remains within these predetermined limits to prevent any potentially explosive situation. Such a photometric analyzer is that sold by E. I. du Pont de Nemours and Company, Inc. as the 400 Analyzer. This device is substantially similar to that described in U.S. Pat. No. 3,306,156 (Glasser et al.) assigned to the assignee of the instant invention. Another device for photometrically monitoring the concentration of chlorine dioxide gas is disclosed in U.S. Pat. No. 4,152,073 (Zimmerman).

There are also available devices whereby the concentration of chlorine may be photometrically measured. However, it is difficult to measure the concentration of chlorine when chlorine dioxide is also present in a stream. This is the case because the chloride dioxide exhibits such a high ultraviolet radiation absorbance characteristic compared to that of chlorine that differentiation of the absorbance characteristics of the chlorine in the presence of chlorine dioxide cannot be effected at comparable concentration levels.

SUMMARY OF THE INVENTION

This invention relates to a method and an apparatus for photometrically analyzing a stream under test containing both chlorine and chlorine dioxide. A first portion of the sample of the stream is photometrically measured and a first signal representative of the chlorine dioxide concentration therein generated. In the preferred embodiment, a second, different, portion of the sample is heated, and the chlorine dioxide therein is decomposed into chlorine and water vapor. This second portion of the sample may be subsequently (or simultaneously with the heating) photometrically analyzed, and a second signal representative of the chlorine concentration therein is generated. The second signal representative of the chlorine concentration in the second sample is functionally related to the concentration of chlorine in the stream under test, to the concentration of chlorine produced by the decomposition of chlorine dioxide in the second sample, and to the dilution, or volumetric increase due to the decomposition of chlorine dioxide in the second sample. Using the first and second signals, a third signal representative of the concentration of chlorine in the stream under test, as well as a fourth signal representative of the ratio of chlorine dioxide to chlorine in the stream under test may be generated by suitable analog or digital circuitry.

BRIEF DESCRIPTION OF THE DRAWINGS

The invention will be more fully understood from the following detailed description thereof, taken in connection with the accompanying drawings, which form a part of this application and in which.

DETAILED DESCRIPTION OF THE INVENTION

Figure 1:
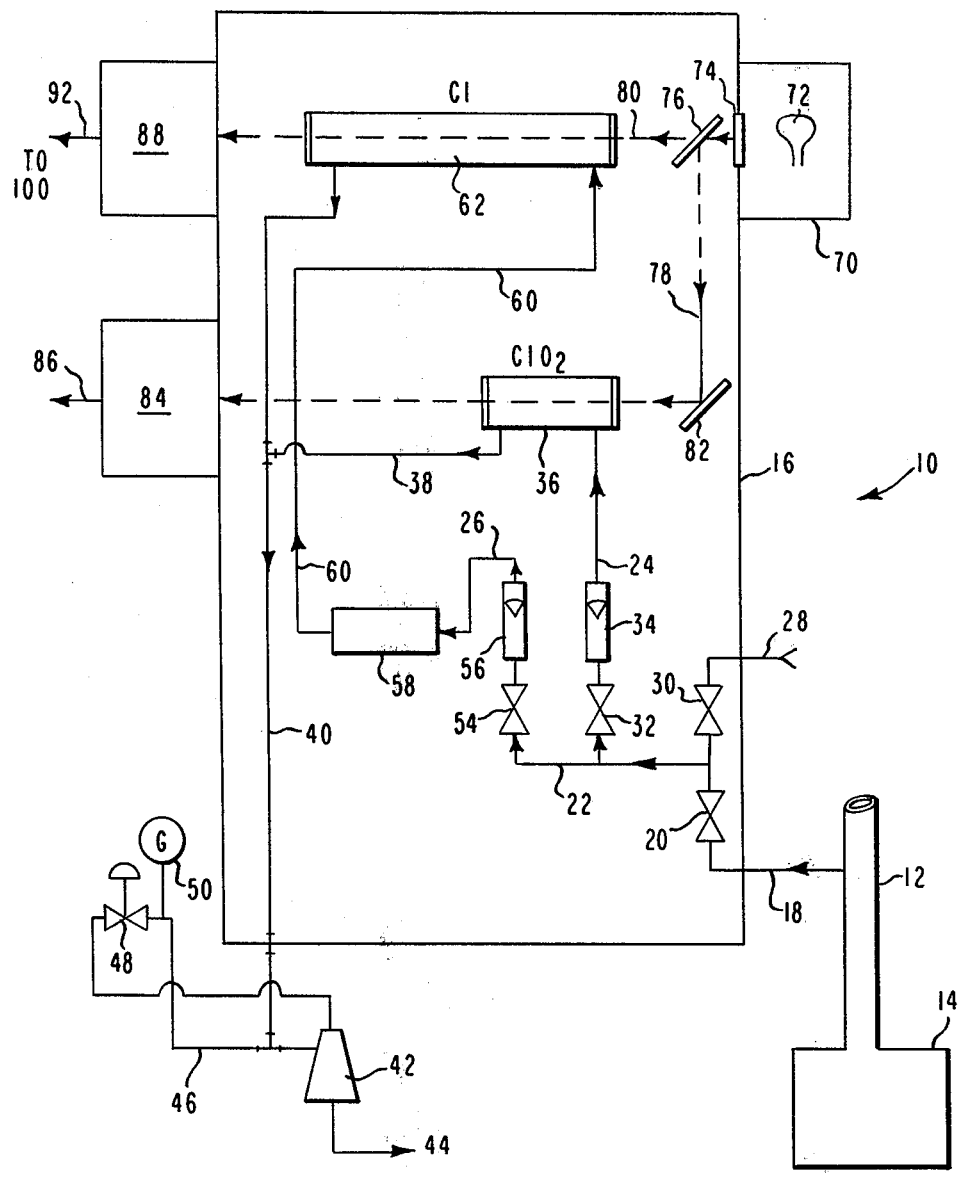
FIG. 1 is a diagrammatic representation of a photometric analysis system for monitoring the concentrations of both chlorine and chlorine dioxide in a stream under test in accordance with the invention; and, FIG. 2 is a functional block diagram of an analog circuit which may be used to generate and process electrical signals representative of the concentrations of chlorine and chlorine dioxide in the stream under test in accordance with the invention.

Throughout the following detailed description, similar reference numerals refer to similar elements in all Figures of the drawings.

FIG. 1 shows a diagram of a photometric analysis system generally indicated by reference character 10 for monitoring the concentrations of both chlorine and chlorine dioxide in a stream under test, such as the effluent stream carried in an outlet pipe 12 from a chlorine dioxide generator diagrammatically illustrated at 14. In the generator 14 chlorate ions are reacted with chlorine and hydrogen ions to produce chlorine and chlorine dioxide in accordance with the following reaction:

$$4H^+ + 2Cl^- + 2ClO_3^- \rightarrow Cl_2 + 2ClO_2 + 2H_2O. \tag{1}$$

The desired end product is chlorine dioxide which is useful, for example, for bleaching pulp in the paper making processes. Under ideal conditions two moles of chlorine dioxide are formed for every mole of chlorine. The system 10 is adapted to photometrically analyze the effluent stream in the outlet pipe 12 so that the concentrations of both chlorine and chlorine dioxide may be monitored to insure that the concentrations of the reaction products lie within acceptable ranges.

Although it is difficult to photometrically analyze a stream under test which contains both chlorine and chlorine dioxide due to the high absorbance characteristic of chlorine dioxide overshadowing that of chlorine, such an analysis may be conducted by the apparatus and method in accordance with the instant invention by making use of the observation that chlorine dioxide decomposes in the presence of heat to form chlorine in accordance with following reaction:

$$2 ClO_2 \xrightarrow{heat} Cl_2 + 2 O_2 \qquad (2)$$

The photometric analysis system 10 in accordance with the instant invention includes a housing 16 into which a sample of the stream under test is conveyed by an inlet conduit or line 18. The line 18 may be interconnected into the outlet pipe 12 from the generator 14 at any convenient predetermined location. A shutoff valve 20 is connected to the line 18. An outlet line 22 leading from the valve 20 splits into a first and a second branch line 24 and 26, respectively. A suitable air line 28 having a shutoff valve 30 therein is connected to the line 22 for zeroing purposes.

The first branch 24 includes a shutoff valve 32 and a flow meter 34 connected to the input end of a flow cell 36. To accommodate the highly corrosive properties of the material in the stream under test, the cell 36 and all other parts wetted by the sample of the stream passed therethrough are fabricated of a fluorethylene polymer material. Any other suitable materials, as other fluorocarbons, titanium or quartz, may be used. The outlet of the cell 36 is connected through a line 38 to an evacuated return line 40. The return line 40 is evacuated by a suitable aspirator 42 and discharged through a line 44. A purging air connection line 46 is connected through a shutoff valve 48 and a pressure gauge 50.

The second branch 26 includes a shutoff valve 54 and a flow meter 56 both similar to the valve 32 and the meter 34, respectively. Any suitable valves and meters may be used. The outlet of the meter 56 is conveyed through a furnace 58. The heated products from the furnace 58 are applied through a line 60 to the inlet of a cell 62 fabricated of the same material as the cell 36 for the same reasons. The cell 62 is longer than the cell 36 since the chlorine absorptivity at the measuring wavelength is less than that of chlorine dioxide at its measuring wavelength. The outlet from the cell 62 is connected to the return line 40.

The furnace 58 is preferably a muffle type furnace with quartz tubing in which the sample of the stream is transported through the furnace. In the furnace 58 a portion of the sample of the effluent is decomposed in accordance with the reaction described in equation (2). It has been found that the furnace 58 should be heated to a temperature greater than 250° C. The temperature of the furnace depends on the residence time of the sample in the furnace, and the temperature of the incoming sample.

Connected to the housing 16 is a lamp housing 70 containing a source 72 of ultraviolet and visible radiation, such as a mercury discharge lamp sold by General Electric Company under model H 100 A4/UV. The spectral output of the radiation source 72 includes at least a reference wavelength and a first and a second indicator wavelength selected in accordance with the material to be photometrically analyzed in the cells 36 and 60. In the present invention, the reference wavelength is 546 nanometers. Also in the present invention, the indicator wavelength for first cell 36 (chlorine dioxide) is 436 nanometers, while the indicator wavelength for the second cell 60 (chlorine) is 313 nanometers.

The ultraviolet and visible energy generated by the source 72 enters the housing through an aperture 74. A beam splitter 76 bifurcates the radiation into a first and a second beam path 78 and 80, respectively. A reflector 82 directs the radiation in the first beam path 78 through the cell 36 into a split beam photometer 84 such as that sold as the 400 Analyzer by E. I. du Pont de Nemours and Company. The photometer 86 is substantially similar to that shown in U.S. Pat. No. 3,306,156 (Glasser et al.), assigned to the assignee of the present invention. The disclosure of this patent is hereby incorporated by reference herein. The output signal from the photometer 84 is carried on an output line 86 and is dependent upon the magnitude of the radiant energy at the indicator wavelength incident upon the photometer 84. This signal is, in turn, dependent upon the concentration of chlorine dioxide in the cell 36.

The radiation of the second beam path 80 passes directly through the second cell 60 into a second photometer 88 similar to the photometer 84. The current output from the photometer 88 is carried on a line 92 and is representative of the absorption of the second indicator wavelength which is dependent upon the concentration of chlorine in the cell 60. Both the photometer 84 and the photometer 88 are disposed in suitable housings mounted to the housing 16. The signals on the lines 86 and 92 are applied to a signal processor arrangement 100.

In operation a test sample of the stream in the pipe 12 is isolated and conducted to the analysis system 10 where it is split into first and second portions which are conveyed along the branches 24 and 26, respectively. The stream under test contains both chlorine dioxide and chlorine and, for the reasons set out earlier, it is advantageous to accurately monitor the concentration of both these materials in the stream under test.

The portion of the sample of the stream under test in the first branch 24 passes through the cell 36 and a first signal representative of the chlorine dioxide concentration therein is generated from the photometer 84 on the line 86.

The portion of the sample of the stream under test in the second branch 26 passes through the furnace 58 and then to the second cell 60. In the furnace 58 the chlorine dioxide in the second portion of the sample is decomposed into its constituents according to the reaction (2). In the furnace 58 the second portion of sample is diluted in accordance with a Dilution Factor defined by the following relation:

$$\text{Dilution Factor} = 1 + \frac{0.5 \, [ClO_2]}{100}, \qquad (3)$$

where [ClO$_2$] is the concentration of chlorine dioxide in the stream under test (and, therefore, in the first portion of the sample) as measured by the photometer 84. The concentration of chlorine in the second portion of the sample is measured by the photometer 88 and a second signal representative thereof is generated on the line 92.

The "final" concentration of chlorine in the second portion of the sample, i.e., after decomposition as measured by the photometer 88, may be expressed in accordance with the relationship:

$$[Cl_2]_{final} = \frac{[Cl_2]_{sample} + 0.5[ClO_2]}{Dilution\ Factor} \quad (4)$$

where [Cl$_2$]$_{sample}$ represents the concentration of chlorine in the sample of the stream under test and the Dilution Factor is derived in accordance with equation (3).

From the relationship shown in equation (4), it directly follows that the concentration of chlorine in the sample of the stream under test may be given by:

$$[Cl_2]_{sample} = [Cl_2]_{final} \cdot (Dilution\ Factor) - 0.5[ClO_2] \quad (5)$$

From the foregoing it may be appreciated that first and second electrical signals on the lines 86 and 92 respectively contain information regarding the concentration of chlorine dioxide in the stream under test (on the line 86) and the "final" concentration of chlorine in the second portion of the sample (on the line 92). However, from both these signals in accordance with equation (4) or equation (5) a signal representative of the concentration of chlorine in the stream under test may be generated. To effect these ends, the signal processing arrangement 100 is provided.

Figure 2:
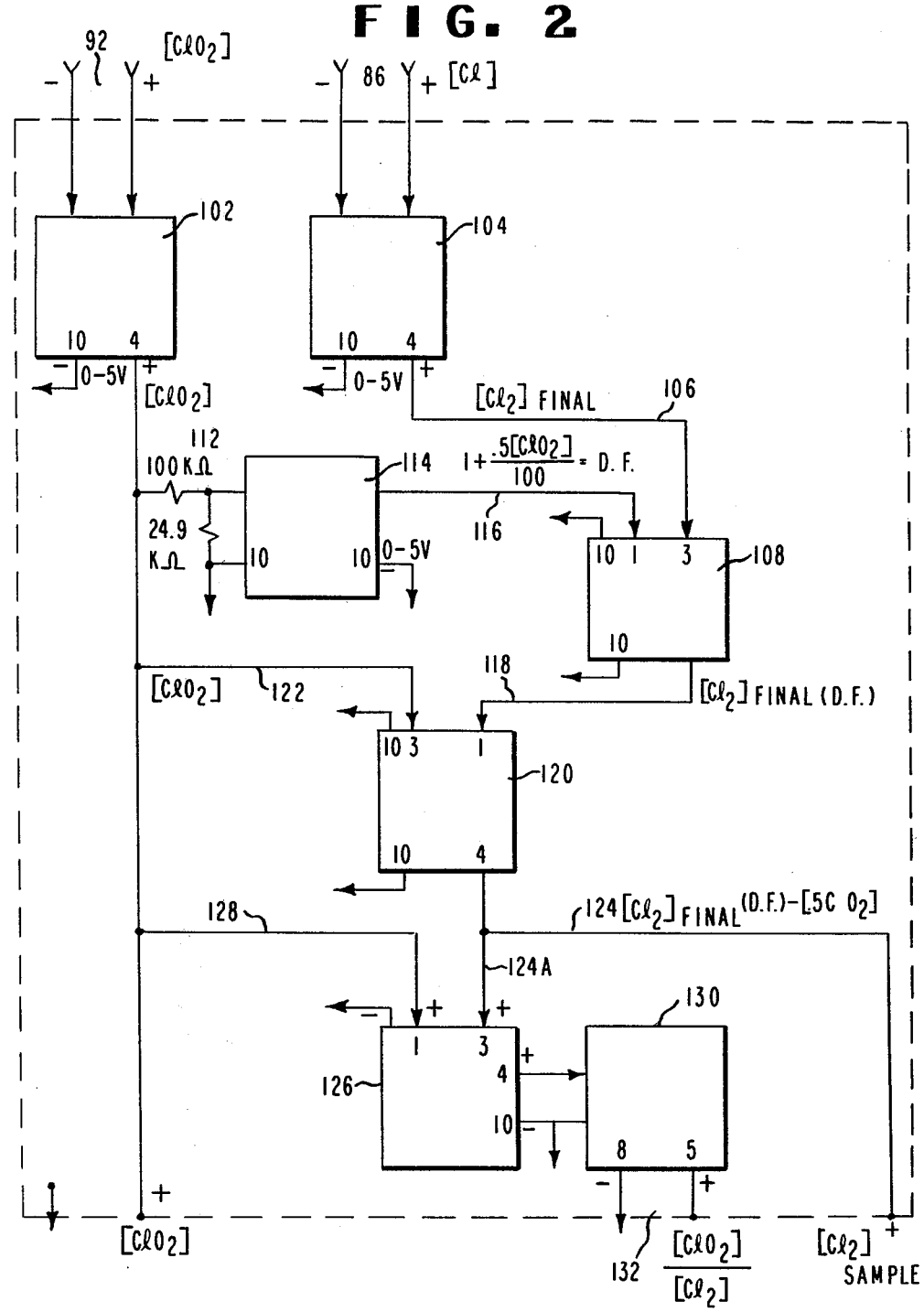

In FIG. 2, a schematic diagram of an analog implementation of the signal processing arrangement 100 is shown. For convenience, the signals carried on various of the lines in the network of FIG. 2 are indicated using the terminology of equation (4) or equation (5). Where appropriate, pin connections on the devices are shown. The first signal on the line 86, representative of the concentration of chlorine dioxide in the sample under test as detected by the first photometer 84, is amplified by an amplifier 102. The second signal, representative of the final (after decomposition) concentration of chlorine in the second portion of the sample under test is amplified by an amplifier 104. Suitable for use as the amplifiers 102 and 104 are devices sold by the Analysis Instruments Division of E. I. du Pont de Nemours and Company under model number 206242.

The output of the amplifier 104 containing a signal representative of the concentration of chlorine in the second portion of the sample is applied over a line 106 to a multiplier element 108 such as that sold by the Analysis Instruments Division of E. I. du Pont de Nemours and Company under model number 206249. The output of the amplifier 102 carrying a signal representative of the concentration of the chlorine dioxide is carried by an output line 110 and applied to an amplifier 114 similar to the amplifiers 102 and 104 but configured as an adder by the provision of the resistor network 112. The value of one of the resistor elements in the network 112 is shown to be 100 K ohms while the value of the resistor R is equal to 0.5 times the full scale range of chlorine dioxide concentration. For example, for a 0–15% chlorine dioxide range, R is equal to 7.5 ohms. The output signal on the line 116 from the adder 114 is representative of the Dilution Factor. The Dilution Factor is the concentration of chlorine in the second portion of the sample taking in account the volumetric increase generated by the decomposition of chlorine dioxide into elemental chlorine and oxygen. The signal on the line 116 is applied to the multiplier 108.

The output of the multiplier 108 is applied to a subtractor element 120 such as that sold by Analysis Instruments Division of E. I. du Pont de Nemours and Company under model number 206244. Also applied to the subtractor 120 over a line 122 is the signal from the amplifier 102 representative of a chlorine dioxide concentration in the first portion of the sample. The output of the subtractor 120 on a line 124 carries a signal representative of the chlorine concentration in the sample. This output may be applied to any suitable meter or visual display apparatus.

Additionally, the output from the subtractor 120 is applied by a line 124A to the input of a divider 126 such as that sold by the Analysis Instruments Division of E. I. du Pont de Nemours and Company under model number 206247. The second input of the divider 126 is derived over a line 128 from the output of the amplifier 102. The divider output is applied through an isolator element 130 such as that sold by the Analysis Instruments Division of E. I. du Pont de Nemours and Company under model number 206246 and the output lines 132 from the isolator 130 carry an electrical signal representative of the ratio of concentrations of chlorine dioxide to chlorine in the sample under test.

Thus, the signal on the line 110 represents the concentration of chlorine dioxide in the sample under test while the signal on the line 124 represents the concentration of chlorine in the sample under test. The ratio of these concentrations is carried on the line 132.

Those skilled in the art, having benefit of the teachings hereinabove set forth, may effect numerous modifications to the instant invention. For example, the analog signal processing network shown in FIG. 3 may be implemented using a microprocessor operating under the control of a program. Alternatively, any other suitable equivalent analog or digital network may be used to effect the electrical manipulation of the signals derived in accordance with the instant invention and in the manner set forth herein. It should be appreciated, however, that such modifications lie within the contemplation of the instant invention as defined in the appended claims.

What is claimed is:

1. A method for photometrically analyzing a stream under test containing both chlorine and chlorine dioxide comprising the steps of:
   (a) photometrically analyzing a first portion of the stream to determine the concentration of chlorine dioxide therein;
   (b) heating a second portion of the stream to a predetermined temperature to decompose any chlorine dioxide therein into elemental chlorine;
   (c) photometrically analyzing the heated second portion of the stream to determine the concentration of chlorine therein taking into account the chlorine produced by the decomposition of the chlorine dioxide and the concomitant dilution produced thereby.

2. The method according to claim 1 further comprising the step of isolating a sample of the stream and thereafter subdividing the sample into the first and second portions.

3. An apparatus for photometrically monitoring a stream under test containing both chlorine and chlorine dioxide comprising:
- a first photometric analyzer for photometrically analyzing a first portion of the stream and for generating a first electrical signal representative of the concentration of chlorine dioxide therein;
- means for heating a second portion of the stream to a predetermined temperature to decompose the chlorine dioxide therein into elemental chlorine; and
- a second photometric analyzer for analyzing the second, heated, portion of the stream and for generating a second electrical signal representative of the concentration of chlorine therein, the second electrical signal being functionally related to the concentration of chlorine produced by the decomposition of the chlorine dioxide in the sample and to the concomitant dilution produced thereby.

4. Apparatus according to claim 3 wherein the heating means comprises a quartz furnace.

5. Apparatus according to claims 3 or 4 further comprising
- means responsive to the first and second signals for generating an electrical signal representative of the ratio of the concentrations of chlorine dioxide to chlorine in the stream under test.

* * * * *